(12) United States Patent
Wallace et al.

(10) Patent No.: US 7,781,708 B2
(45) Date of Patent: Aug. 24, 2010

(54) SYSTEM FOR INDUCTIVE HEATING OF WORKPIECE USING COILED ASSEMBLIES

(75) Inventors: Trevor Wallace, Huntington Beach, CA (US); Kurt D Hand, Crown Point, IN (US); John P Kearns, League City, TX (US)

(73) Assignee: Team Industrial Services, Inc., Alvin, TX (US)

( * ) Notice: Subject to any disclaimer, the term of this patent is extended or adjusted under 35 U.S.C. 154(b) by 0 days.

(21) Appl. No.: 12/154,623

(22) Filed: May 23, 2008

(65) Prior Publication Data

US 2009/0291018 A1    Nov. 26, 2009

(51) Int. Cl.
*H05B 6/44*    (2006.01)

(52) U.S. Cl. .................... 219/656; 219/674; 422/292

(58) Field of Classification Search .................. 422/1, 422/292; 219/600, 673, 674, 675, 676, 656
See application file for complete search history.

(56) References Cited

U.S. PATENT DOCUMENTS

| 3,301,991 | A | * | 1/1967 | Springob et al. | 219/637 |
| 5,317,121 | A | * | 5/1994 | Katayama et al. | 219/672 |
| 5,495,094 | A | * | 2/1996 | Rowan et al. | 219/645 |
| 6,555,801 | B1 | * | 4/2003 | LeMieux et al. | 219/656 |

OTHER PUBLICATIONS

Team Industrial Services, Inc., Heat Decon Proposal for TVA Pine Bluff Project RFP 685361, Oct. 12, 2006, 41 pgs.
Tennessee Valley Authority Contract No. 59527, Pine Bluff Arsenal, Arkansas, Heating Ton Containers, Apr. 5, 2007, 39 pgs.

* cited by examiner

*Primary Examiner*—Sean E Conley
(74) *Attorney, Agent, or Firm*—Howrey LLP

(57) ABSTRACT

A system for inductively heating a workpiece including a heating coil that surrounds the sides and ends of the workpiece, wherein the heating coil comprises a first coil assembly that encloses a first portion of the workpiece and a second coil assembly that encloses a second portion of the workpiece. A power supply is operatively connected to the first coil assembly and the second coil assembly.

6 Claims, 4 Drawing Sheets

SYSTEM FOR INDUCTIVE HEATING OF WORKPIECE USING COILED ASSEMBLIES

BACKGROUND OF THE INVENTION

The present invention relates generally to a method and system for inductively heating a workpiece, and more specifically to a method and system for inductively heating a workpiece by a plurality of coiled tubing assemblies.

There are many different approaches in heating a "workpiece" (the material to be heated), and the selected approach depends on many considerations, such as the purpose for the heating, size and specifications of the workpiece, power requirements, and time limitations for the heating process. A few commonly known methods for heating a workpiece include the use of electrical resistance, combustion, and induction. The electrical resistance method generally involves the creation of heat by the flow of electric current through a conductor or element of high resistance. A disadvantage of this method is that it is usually limited to heating smaller workpieces or localized areas on larger workpieces due to the large power requirement and lengthy time to wrap wire and heating elements around the workpiece. Another disadvantage is the fact that the conductor itself becomes very hot, thereby increasing the potential for injury during operation. The combustion method generally involves the creation of heat by the exothermic reaction between a fuel and an oxidant. A disadvantage of this method is that it is usually limited to large workpieces that do not need finite temperature control and heat placement. The induction technique creates heat by applying an induced magnetic field around the workpiece that creates resistance (and heat) in the workpiece. There are many advantages of induction heating over other traditional heating techniques, such as quick heating of the workpiece, heating without direct contact between the coil and the workpiece, narrowly focused heat application, consistent and improved heating results, and efficient power consumption.

In general, the basic principles of induction and the techniques for heating a workpiece through an induction method are well known. It is presently thought that the induction technique heats the workpiece by the result of hysteresis and eddy current losses in the workpiece. Thus, magnetic workpieces are easier to heat than non-magnetic workpieces. The induced magnetic field is created by wrapping a coil around the workpiece and supplying a high frequency alternating current by a remote power source to the coil to create an alternating magnetic field around the workpiece. The frequency of the requisite alternating current depends on the workpiece's size, material type, and coupling (interaction between the workpiece and the coil), and the desired penetration depth of the created heat in the workpiece. The coil is typically made of copper tubing (or another material with good conductivity) and is cooled with a fluid such as water. The diameter, shape, and number of turns of the coil influence the efficiency and field pattern of the magnetic field.

Induction heating has a wide range of heating applications, such as surface hardening, melting, brazing, and soldering. In general, dedicated heating coils can be designed and manufactured for small and regularly shaped workpieces. For example, small rigid heating coils have been designed to heat small components in the automobile industry or small pipes in the steel fabrication industry. As the workpiece is increased in size and/or irregularity in its shape, the design and manufacture of an effective heating coil to produce the required temperature and/or heating profile in the container becomes problematic.

Large metal containers are often used to hold a wide variety of toxic chemicals, such as mustard, lewisite, nerve agents, and various commercial chemicals. Once the chemical is removed from the container, the container still has traces of its previous contents that need to be removed. It is known in the industry that large, metal cylindrical containers that previously held toxic or contaminated chemicals can be decontaminated using induction heating with flexible coils, as shown in FIG. 1. Typically, multiple thermocouples are spot welded on a container in predefined locations for the subsequent monitoring of the container's temperature. A layer of thermal insulation is wrapped around the container to mitigate heat losses from the container as it is heated and to protect the heating coils. A long, flexible coiled tubing is then cylindrically wrapped around the shell face of the insulated container. Because the diameter, shape, and number of turns of the coil influence the efficiency and field pattern of the magnetic field, the flexible coil must be properly-positioned on the container to achieve the optimal magnetic field. A power source supplies an alternating current to the coil that creates resistance in the container as a result of the applied and changing magnetic field. The amount of heating in the container increases as the supplied power increases, and as a result, the supplied power can be adjusted to heat the container to the desired temperature and/or heating profile.

Although this method of "flexible coil" induction heating has been used in industry, it suffers from numerous and significant disadvantages. One primary disadvantage is that installation of the flexible coil around the container is not only time and labor intensive but is prone to inconsistencies. Each wrap of the flexible coil must be operatively positioned next to the adjacent wrap to create an effective magnetic field. This positioning includes not only the distance between each wrap of coiled tubing, but the pitch (or angle) and tightness of the flexible coil around the container. It is a long and laborious process to individually wrap and position the flexible coil around the container, and the placement and effectiveness of the flexible coil often varies significantly between each container as a result of inconsistencies and installation error. The inconsistent spacing between adjacent coil wraps is illustrated in FIG. 1. Another common problem is that there is no good way to heat the ends of the container with the use of the traditional flexible coil method. In the case of a cylindrical container, the flexible coil can (with enough time and labor) be wrapped around the shell face of the container, but it is very difficult to wrap the end faces of the cylindrical container with flexible coils, and much more difficult to wrap the end face with any type of precision and consistency. Usually, the end faces are not even wrapped. The unwrapped end faces further provides for inconsistent and ineffective heating results of the container, and as a result, the container cannot be efficiently and/or effectively decontaminated.

What is needed is a system and method for inductively heating a workpiece that will significantly reduce coil installation time, provide a more efficient design for power and heating time limitations, provide efficient heating to all desired portions of the workpiece, and provide a more standardized coil spacing for repetitive heating and temperature uniformity in the workpiece.

SUMMARY OF THE INVENTION

In one aspect, a system for inductively heating a workpiece is disclosed, comprising a heating coil, wherein the heating coil comprises a first coil assembly that encloses a first portion of the workpiece and a second coil assembly that encloses a second portion of the workpiece. A power supply is operatively connected to the first coil assembly and the second coil assembly.

Also disclosed is a method for inductively heating a workpiece, comprising enclosing the workpiece with a plurality of coil assemblies and providing power to at least one of the plurality of coil assemblies.

Also disclosed is a method for decontaminating a container, comprising enclosing the container with a plurality of coil assemblies, enclosing a shell face portion and an end face portion of the container with at least one of the plurality of coil assemblies, and providing power to at least one of the plurality of coil assemblies to decontaminate the container.

Also disclosed is a system for inductively heating a workpiece comprising a heating coil surrounding each side and each end of the workpiece.

DETAILED DESCRIPTION OF THE PREFERRED EMBODIMENT OF THE INVENTION

Figure 1:
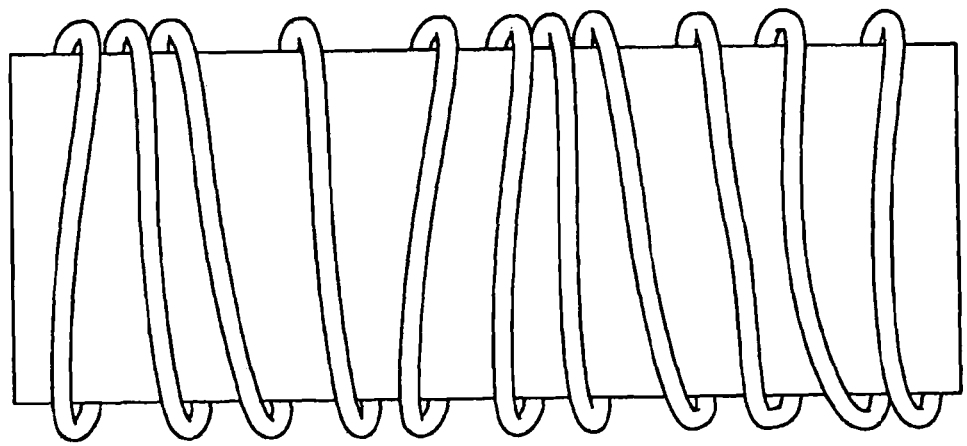
FIG. 1 shows a typical prior art flexible coil used in the induction heating of a container.
Figure 2:
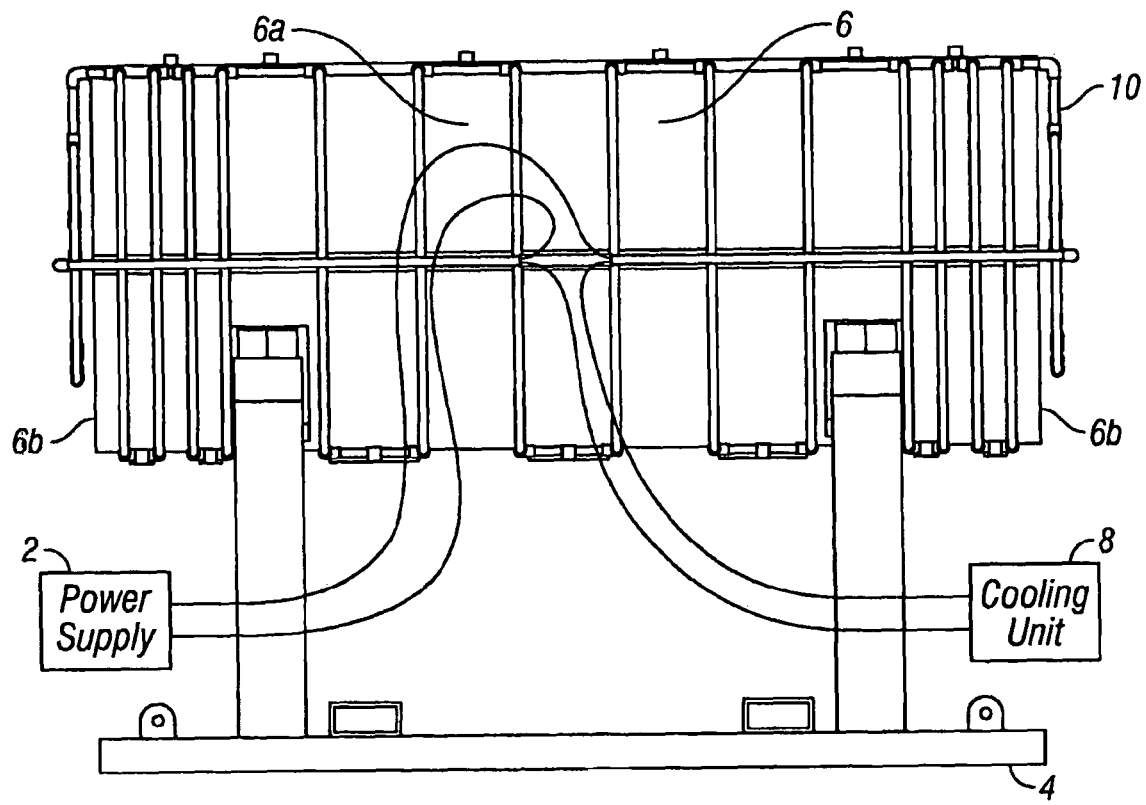
FIG. 2 illustrates a preferred embodiment of the present invention including a side view of a support cradle, container, and heating coil, and also a power supply and cooling unit.

Referring to FIG. 2, a preferred embodiment of the present invention is illustrated. FIG. 2 shows a power supply 2, a support cradle 4, a container 6, a cooling unit 8, and a heating coil 10. The power supply 2 supplies a high frequency alternating current to the heating coil 10, and can be any commercially available induction heating unit (for example, a portable 35-kW induction heating unit with a 60-amp, 480-VAC, 3 phase power supply). The power supply 2 induces a magnetic field around the container 6, and the output of the power supply 2 determines the speed and degree at which the container 6 can be heated. It is well known in the art that the specifications of the power supply 2 depend upon the specifications of the container 6 and the specific heating application (such as surface hardening, melting, brazing, soldering, heating to fit, and decontamination). The support cradle 4 is made to support the container 6 before, during, and/or after heating the container 6. The support cradle 4 is designed for forklift access to the container 6 and utilizes fire-bricks arranged into effective V-blocks contained in two steel saddles on a common box-beam base. The container 6 is a cylindrical vessel with a side or shell face 6a and two end faces 6b, but any workpiece that is affected by a magnetic field can be heated by a preferred embodiment of this invention. The cooling unit 8 is any commercially available cooling unit that can pump a fluid (such as glycol ethylene, available from commercial welding supply outlets) through the heating coil 10. It is well known in the art that the specifications of the cooling unit 8, and the flow rate and amount of coolant, depend upon the dimensions of the heating coil 10, the power supplied to heating coil 10, and the specific heating application. Further, an air filtration unit (not shown) can be utilized according to procedures well known in the art to collect and direct gas and smoke vented from the container 6 when heated, such as a smoke eater air handling system commonly found in weld shops. The air filtration unit and cooling unit 8 require a source of power, but may or may not be connected to the power supply 2. The heating coil 10 is designed to enclose (or surround) the portions of the container 6 that are to be heated. For optimal results, the specifications of the heating coil 10 should generally reflect the shape of the container 6 and other variables and limitations in the heating process, such as power requirements, the desired temperature and/or heating profile in the container, heating time requirements, and the specific heating application. The tolerance in the heating coil design decreases as the requirements in the heating process become more stringent and numerous. With an effective heating coil design, a desired heating profile in the container 6 is achieved and the efficiency of the power supply 2 is maximized.

Figure 3:
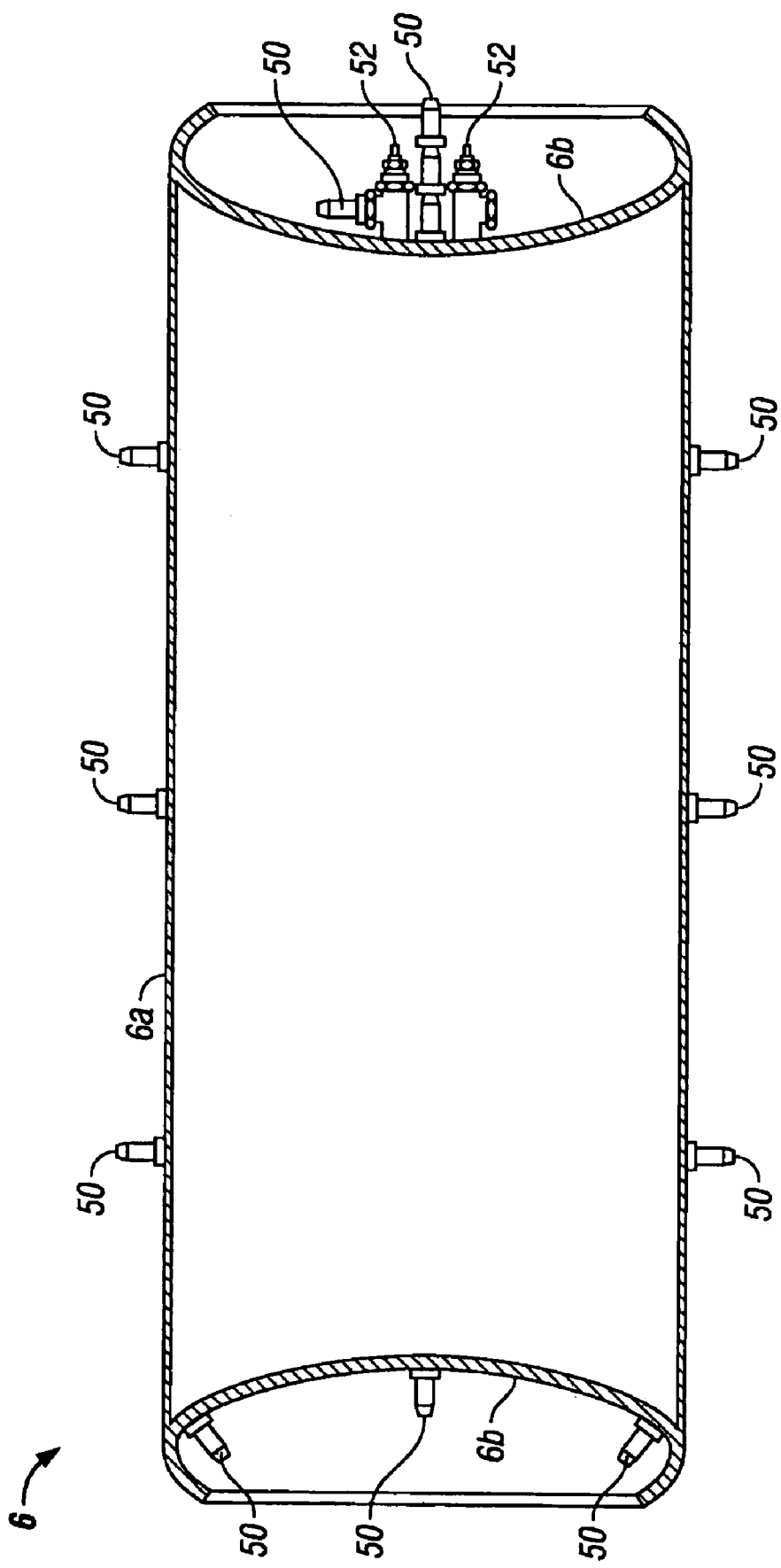
FIG. 3 illustrates a cross-sectional side view of the container shown in FIG. 2.

Referring to FIG. 3, a cross-sectional view of the container 6 is illustrated. Any workpiece that is affected by a magnetic field can be enclosed in the heating coil 10 and subsequently heated by a preferred embodiment of this invention. As an example, the container 6 is a cylindrical vessel with a shell face or side of the container 6a and two end faces of the container 6b. The container 6 may have irregularly shaped end faces, such as the concave end faces 6b shown in FIG. 3. The container 6 has an outer diameter of 30.5 inches, an overall length of 82 inches, a shell thickness of $13/32$-inch, an end-face thickness of $3/4$-inch, and is made of carbon steel. Container 6 may have a valve assembly 52 attached on one or more of the end faces 6b that allows for the input and output of fluids to the container 6. Sensors 50 may also be attached to the container 6 for the measuring of temperatures on or in the container 6. One of skill in the art will appreciate that a wide variety of sensors 50 can be used, such as Type K quartz/quartz 20-guage thermocouples, and that the location and attachment of these sensors depends on the specifications of the container 6 and the specific heating application.

Figure 4:
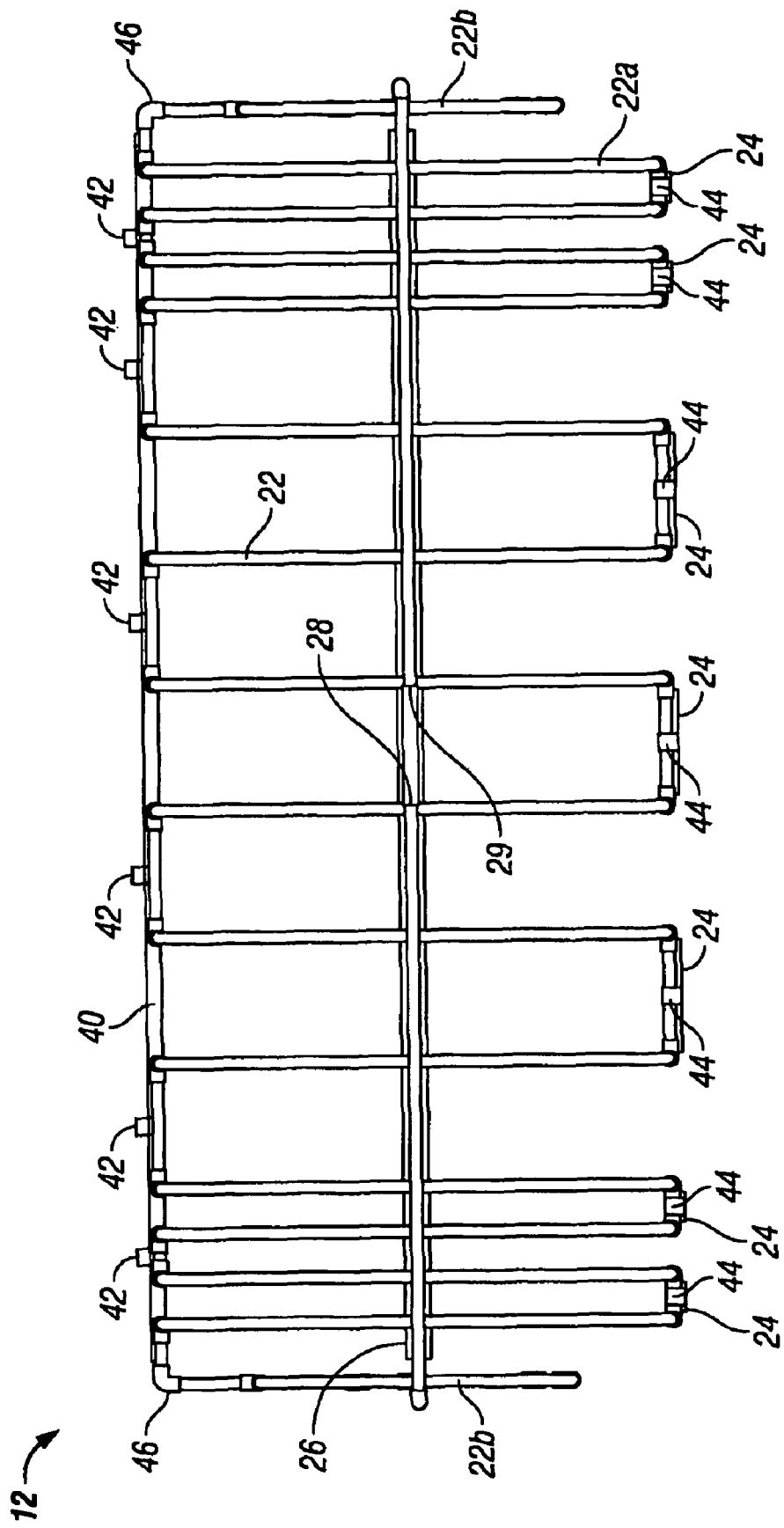
FIG. 4 illustrates a side view of a preferred embodiment of the heating coil shown in FIG. 2.
Figure 5A:
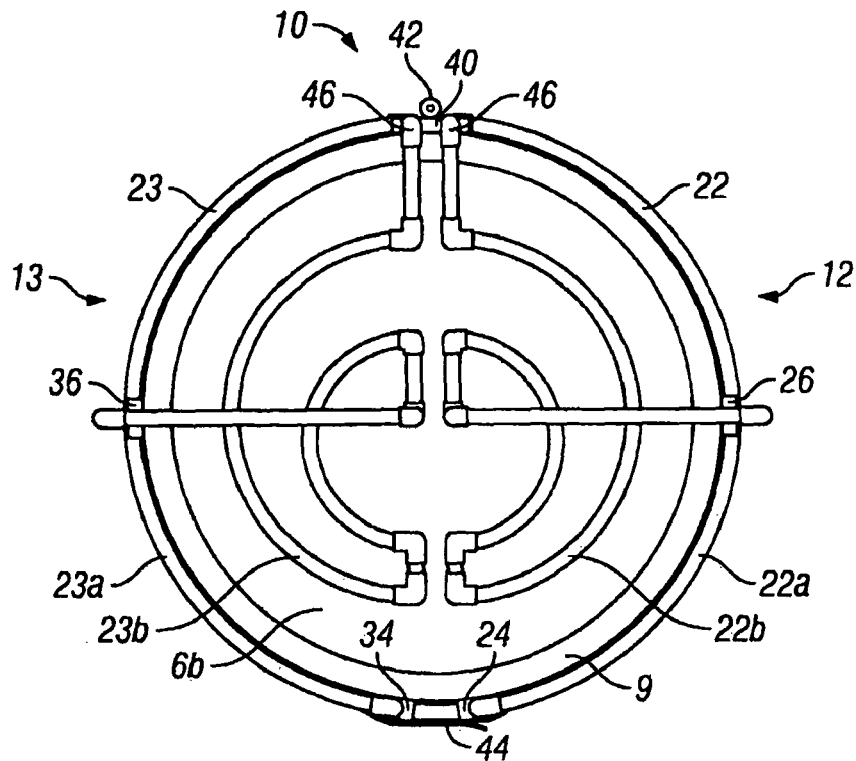
FIGS. 5a and 5b illustrate an end view of a preferred embodiment of the heating coil shown in FIG. 2 surrounding the container.
Figure 5B:
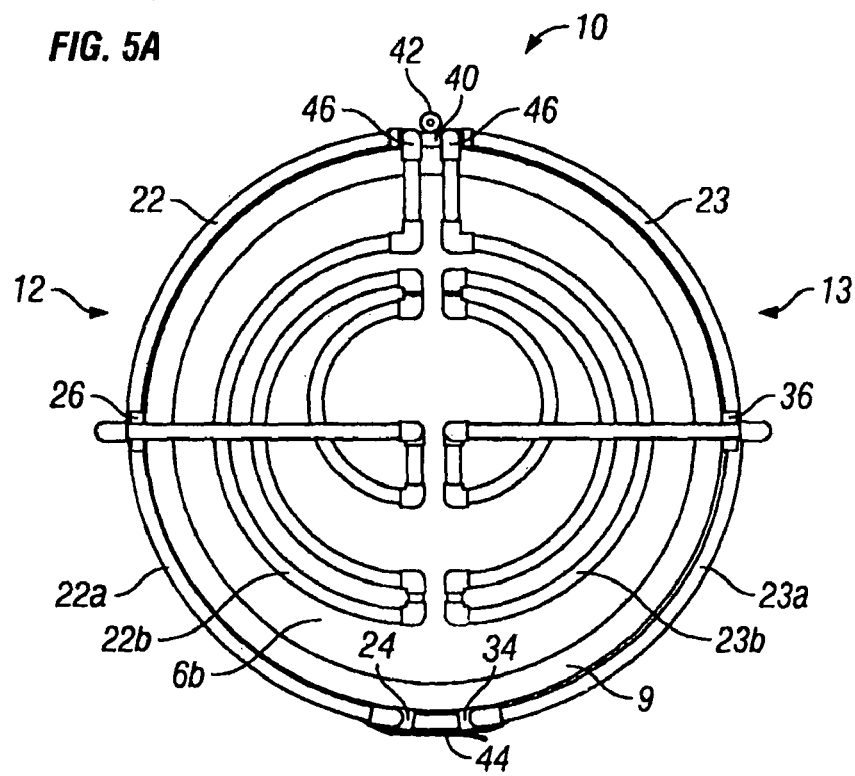

FIG. 4 illustrates a preferred embodiment of a side view of the heating coil 10 and FIGS. 5a and 5b illustrate end views of a preferred embodiment of the heating coil 10. The heating coil 10 consists of a first coil assembly 12 and a matching, second coil assembly 13 (shown in FIG. 5). The first coil assembly 12 and the second coil assembly 13 are designed to enclose (or surround) the container 6 in a way that generally reflects the shape of the container 6 and other variables in the heating process. For instance, a distance of approximately 1-2 inches between the first and second coil assemblies 12 and 13 and the container 6 offers adequate clearance between the heating coil 10 and the container 6 while still being able to efficiently heat the container 6. In a preferred embodiment, the first coil assembly 12 and the second coil assembly 13 are arranged to provide a substantially uniform temperature profile in the container 6 when heated. The uniformity of the profile depends on the specific heating application and the desired portions of the workpiece to be heated. For example, temperature measurements of the container 6 may vary between the sensors 50 by 20% of a container and still be considered substantially uniform in certain heating applications, whereas other heating applications may allow temperatures measurements in the container to vary only by 1-5%. The heating profile of the container 6 can be monitored by receiving a temperature from each of the sensors 50. In a preferred embodiment, each temperature measurement from sensors 50 should be the minimal temperature required for the specific heating application. In other instances, the temperature of the container 6 may be calculated by averaging each of the temperature measurements from sensors 50.

Referring to FIGS. 5a and 5b, a preferred embodiment of the end views of the heating coil 10 around container 6 is illustrated. The first coil assembly 12 utilizes a first turned coiled tubing section 22 that encloses approximately one half of each end face of the container 6b and approximately one half of the shell face of the container 6a. Although one of skill in the art will appreciate that many sizes and types of tubing can be utilized, the tubing is typically made of copper or another material with good conductivity, is coated in a non-conductive material (such as glyptal varnish, a dielectric paint), and has a diameter of ¾-inches. The first turned coiled tubing section 22 contains a first input section 28 and a first output section 29. The first input section 28 is connected to the input connections of the power supply 2 and cooling unit 8 (shown in FIG. 2). The first output section 29 is connected to the output connections of the power supply 2 and cooling unit 8. As a result, the first turned coiled tubing section 22 is directly connected to power supply 2 and directly connected to cooling unit 8. Likewise, the second coil assembly 13 utilizes a second turned coiled tubing section 23 with a second input section and second output section (not shown), and is directly connected to power supply 2 and cooling unit 8.

In a preferred embodiment, the first coil assembly 12 utilizes first lower support bars 24 and a first side support bar 26 and the second coil assembly 13 utilizes second lower support bars 34 and a second side support bar 36. The support bars can be made of any non-metallic material that provides rigidity to the enclosure around the container 6, such as Mika (available from industrial electrical supply outlets). One of skill in the art will appreciate that the first coil assembly 12 and second coil assembly 13 can be attached and/or fastened together by a variety of techniques. In a preferred embodiment, the first coil assembly 12 and second coil assembly 13 are attached using hinges 42 attached to an upper support bar 40 and first coil assembly 12 and second coil assembly 13. Opposite hinges 42, the first coil assembly 12 can be fastened to the second coil assembly 13 by any common fasteners 44, such as by Velcro strips, nylon ties, flexible cords or other non-conductive fastening devices installed on the lower support bars 24 and 34.

The first turned coiled tubing section 22 and second turned coiled tubing section 23 utilize specifications that generally reflect the shape and material of the container 6. Specifically, the diameter, shape, position, and number of turns in the coiled tubing sections influence the efficiency and effectiveness of the heating process. The design of the coiled tubing sections generally should be arranged to provide the desired heating profile in the container 6 when heated. One of skill in the art will appreciate that more turns of the coiled tubing sections may be necessary around portions of the container 6 where more heat is required, such as portions of the container 6 with a greater wall thickness. With the coiled tubing sections generally designed to reflect the shape of the workpiece and a desired heating profile, and with the size and type of tubing and/or supports bars utilized in a preferred embodiment of this invention, the enclosure around the workpiece is rigid and the coiled turns in the coiled tubing sections are fixed and/or standardized relative to each other and the workpiece.

In a preferred embodiment, the first turned coiled tubing section 22 encloses a shell face or side portion of the container 6a with a first shell face coiled tubing section 22a and encloses a portion of each end face of the container 6b with first end face coiled tubing section 22b. Similarly, the second turned coiled tubing section 23 encloses a shell face or side portion of the container 6a with a second shell face coiled tubing section 23a and encloses a portion of each end face of the container 6b with second end face coiled tubing section 23b. In this particular embodiment, the distance between the turns in the coiled tubing sections enclosing the shell face of the container 6a decrease towards the end faces of the container 6b (see FIG. 4) because the thickness of the container 6 increases towards its ends and the more closely spaced coils impart more heat to compensate for the increased contained thickness. Other coil designs are of course possible. In this example, the rows of the shell face coiled tubing section 22 are approximately 8" apart in the middle of the shell face and approximately 3" apart near the end of the shell face. The turns in the end face coiled tubing sections are concentrically arranged to the shell perimeter and are designed to provide the desired heating profile in the end faces of the container 6b while allowing outlet valves to be inserted on the end face (See FIGS. 5a and 5b). Containers may have irregularly shaped end faces (such as pointed, convex, or concave end faces), and in these instances, the end face coiled tubing sections 22b and 23b may have to be adjusted to better enclose the end face of the container 6b. Adjustors 46 may be utilized between the end face coiled tubing sections and the shell face coiled tubing sections that allow the end face coiled tubing sections to be positioned (by adjusting, bending, sliding, or flexing) to better enclose the end face of the container 6b for a more efficient heating of the container 6. For example, the adjustors 46 may be flexible connectors that can be bent to position the end face coiled tubing sections to approximately 1-1.5 inches away from the end face of the container 6b. Insulation 9 (shown in FIGS. 5a and 5b) is commonly available thermal insulation that can be installed between the container 6 and the heating coil 10 and is used to mitigate heat losses from the container 6 as it is heated and to protect the heating coil 10. By way of example, the insulation 9 can be 2-inch thick Pyro Shield insulation blankets consisting of 10 lb/ft$^3$ density PyroSil 2000 silica needled mat core encased in ¹⁄₁₆-inch thick stitched jacket of 3-dimensional weave, 40 oz/yd$^2$ silica cloth.

In another preferred embodiment, a method is used to inductively heat a workpiece according to the following procedure. In operation, sensors 50 are spot-welded in a procedure well known to those of skill in the art and at a location on the workpiece in the following pattern (shown in FIG. 3): one to three thermocouples along the top of the workpiece, one to three thermocouples along the bottom of the workpiece, one to three thermocouples equally spaced vertically on one end face of the workpiece, one to three thermocouples equally spaced horizontally along the other end face of the workpiece, one thermocouple on the valve assembly 52, and one thermocouple on insulation 9. A forklift positions the workpiece on support cradle 4 after insulation 9 is placed on the support cradle 4. Insulation 9 is then installed on the workpiece by wrapping individual insulation blankets around the workpiece and fastening with Velcro strips. The heating coil 10 is enclosed around the workpiece and insulation 9 by closing the first coil assembly 12 around a first half of the workpiece and closing the second coil assembly 13 around a second half of the workpiece. The heating coil 10 is fastened together by attaching a plurality of the first lower support bars 24 to the second lower support bars 34 by Velcro strips 44. The end face coiled tubing sections can be arranged to better enclose the end faces of the workpiece by bending adjustors 46 and positioning the end face coiled tubing sections to a distance of approximately 1-1.5 inches from the end faces 6b.

Cables from power supply 2 (a 35 kW portable induction heating unit) are connected to the first input section 28 and first output section 29 of the first coil assembly 12, and additional cables from the power supply 2 are connected to the second input section and second output section of the second coil assembly 13. Input and output tubing from cooling unit 8 are connected to the first input section 28 and first output section 29 of the first coil assembly 12, and additional input and output tubing from the cooling unit 8 are connected to the second input section and second output section of the second coil assembly 13. The sensors 50 are connected to sensor cables of a data acquisition device (that may or may not be part of the power supply 2) that obtains, monitors, and/or records temperature readings from the sensors 50.

The power supply 2 is adjusted to provide the necessary amount of power to the heating coil 10 to reach a temperature in the workpiece required for the specific heating application. One of skill in the art will appreciate that the size of the power supply 2, the amount and duration of power delivered from the power supply 2, and the temperature of the container 6 depends on multiple considerations, including the specific heating application, the specifications of the workpiece, the specifications of the heating coil 10, and the contents and prior contents of the workpiece. Cooling unit 8 is a closed loop cooling system with multiple outlets and inlets to circulate the glycol ethylene coolant in heating coil 10 and includes at least a coolant reservoir, a coolant pump, a heat exchanger to cool the coolant after passing through the heating coil, and a fan motor to cool the cooling unit. It is well known in the art that the specifications of the cooling unit 2, and the flow rate and amount of coolant, depend upon the dimensions of the heating coil 2 and the specific heating application.

In another preferred embodiment, a method is provided to thermally decontaminate a container. Following the same assembly procedure detailed above, a power supply 2 (a portable 35 kW induction heating unit) is used to provide power to the first coil assembly 12 and second coil assembly 13. The power provided by the induction heating unit to the heating coil 10 is adjusted according to the temperature and/or heating profile required in the container 6 to effectively decontaminate the container 6. The following is an example of a temperature-time heating profile to effectively decontaminate the container 6 by achieving the U.S. Army criteria for a 5× decontamination rating: the container is heated from ambient temperature to approximately 250-275° F. and held at that temperature for at least 15 minutes; the container is then heated to approximately 450° F. and held at that temperature for at least 15 minutes; the container is then heated to approximately 1025-1150° F. and held at that temperature for at least one hour. In a preferred embodiment, each measured temperature from sensors 50 should indicate a temperature that is at least 1000° F. within approximately 3.5-4 hours. Once the container 6 has been effectively decontaminated to the required level (such as the 5× decontamination rating), the power supply 2 to the heating coil 10 can be turned off.

It will be apparent to one of skill in the art that described herein is a novel system and method for inductively heating a workpiece with a plurality of coiled tubing assemblies. While the invention has been described with references to specific preferred and exemplary embodiments, it is not limited to these embodiments. For example, in addition to decontaminating a container, the plurality of coiled tubing assemblies can be use to enclose a workpiece in a wide range of induction heating applications, such as surface hardening, melting, brazing, and soldering. The invention may be modified or varied in many ways and such modifications and variations as would be obvious to one of skill in the art are within the scope and spirit of the invention and are included within the scope of the following claims.

What is claimed is:

1. A system for inductively heating a workpiece, the system comprising:
   a cradle to support the workpiece, the workpiece having a side face and two end faces;
   a heating coil which encloses the workpiece, the cradle being located below the workpiece;
   a heating coil comprising:
     an upper support bar located above the workpiece;
     at least one rotation mechanism attached to the upper support bar;
     a first coil assembly that encloses approximately half of the side face and approximately half of each of the end faces of the workpiece; and
     a second coil assembly that encloses a remaining portion of the side face and a remaining portion of each of the end faces of the workpiece, wherein an upper end of the first and second coil assemblies are attached to the rotation mechanism; and
   at least one fastener attached to a bottom end of the first and second coil assemblies, the fastener being adapted to fasten the bottom end of the first coil assembly to the bottom end of the second coil assembly; and a power supply operatively connected to the first coil assembly and the second coil assembly.

2. A system as defined in claim 1, the system further comprising an adjustor attached to a portion of each of the first and second coil assemblies which encloses the end faces of the workpiece, the adjustor being adapted to adjust the first and second coil assemblies to a distance of 1-1.5 inches from the end faces of the workpiece.

3. A system as defined in claim 1, wherein the system is arranged to provide a substantially uniform heating profile in the workpiece.

4. A system as defined in claim 1, wherein the heating coil is rigid.

5. A system as defined in claim 1, the system further comprising sensors which measure the temperature of the workpiece.

6. A system as defined in claim 1, wherein the first and second coil assemblies are arranged to heat each surface area of the workpiece.

* * * * *